United States Patent
Kim et al.

(10) Patent No.: US 11,684,793 B2
(45) Date of Patent: Jun. 27, 2023

(54) NON-THERMAL ATMOSPHERIC-PRESSURE PLASMA KELOID TREATMENT DEVICE, AND USE THEREOF

(71) Applicant: AJOU UNIVERSITY INDUSTRY-ACADEMIC COOPERATION FOUNDATION, Suwon-si (KR)

(72) Inventors: Chul Ho Kim, Seoul (KR); Sung Un Kang, Suwon-si (KR)

(73) Assignee: AJOU UNIVERSITY INDUSTRY-ACADEMIC COOPERATION FOUNDATION, Suwon-si (KR)

(*) Notice: Subject to any disclaimer, the term of this patent is extended or adjusted under 35 U.S.C. 154(b) by 559 days.

(21) Appl. No.: 16/648,883

(22) PCT Filed: Jul. 27, 2018

(86) PCT No.: PCT/KR2018/008518
§ 371 (c)(1),
(2) Date: Mar. 19, 2020

(87) PCT Pub. No.: WO2019/022553
PCT Pub. Date: Jan. 31, 2019

(65) Prior Publication Data
US 2020/0269061 A1 Aug. 27, 2020

(30) Foreign Application Priority Data
Jul. 28, 2017 (KR) .......................... 10-2017-0096163

(51) Int. Cl.
| | |
|---|---|
| *C07H 21/04* | (2006.01) |
| *C07H 21/02* | (2006.01) |
| *A61N 1/44* | (2006.01) |
| *A61P 17/02* | (2006.01) |
| *A61K 31/713* | (2006.01) |
| *H05H 1/24* | (2006.01) |
| *C12N 15/113* | (2010.01) |
| *A61K 48/00* | (2006.01) |
| *A61M 11/00* | (2006.01) |

(52) U.S. Cl.
CPC .............. *A61N 1/44* (2013.01); *A61K 31/713* (2013.01); *A61K 48/00* (2013.01); *A61P 17/02* (2018.01); *C12N 15/1138* (2013.01); *H05H 1/24* (2013.01); *A61M 11/00* (2013.01); *H05H 2245/30* (2021.05)

(58) Field of Classification Search
CPC .................................................... C12N 15/113
See application file for complete search history.

(56) References Cited

FOREIGN PATENT DOCUMENTS

| | | |
|---|---|---|
| JP | 2011-000224 A | 1/2011 |
| JP | 2014-212839 A | 11/2014 |
| JP | 2015-084290 A | 4/2015 |
| KR | 10-1577207 B1 | 12/2015 |
| KR | 10-2016-0072759 A | 6/2016 |
| KR | 10-2017-0081962 A | 7/2017 |
| KR | 10-1773846 B1 | 9/2017 |
| KR | 10-1773847 B1 | 9/2017 |
| KR | 10-2017-0135216 A | 12/2017 |
| WO | 2007/013852 A1 | 2/2007 |

OTHER PUBLICATIONS

Sung Un Kang et al., "Opposite Effects of Non-thermal Plasma on Cell Migration and Collagen Production in Keloid and Normal Fibroblasts", PLOS ONE, Nov. 16, 2017, pp. 1-14.
International Search Report for PCT/KR2018/008518 dated Oct. 19, 2018 [PCT/ISA/210].
International Preliminary Report on Patentability for PCT/KR2018/008518 dated Oct. 19, 2018.

*Primary Examiner* — Amy H Bowman
(74) *Attorney, Agent, or Firm* — Sughrue Mion, PLLC

(57) ABSTRACT

The present invention relates to a non-thermal atmospheric-pressure plasma keloid treatment device and a use thereof. The non-thermal atmospheric-pressure plasma keloid treatment device according to the present invention has effects of inhibiting collagen deposition in keloid fibroblasts and mobility thereof, and thus, is expected to be greatly useful for preventing and treating keloids.

5 Claims, 15 Drawing Sheets
Specification includes a Sequence Listing.

NON-THERMAL ATMOSPHERIC-PRESSURE PLASMA KELOID TREATMENT DEVICE, AND USE THEREOF

STATEMENT OF GOVERNMENTAL SUPPORT

The invention was made with government support under Serial No. 2017M3A9F7079339 awarded by the Ministry of Science and ICT (Republic of Korea), No. 1485019434 (based on 2023 number) awarded by Ministry of Environment (Republic of Korea), No. 2023R1A2C3002835 awarded by Ministry of Science and ICT (Republic of Korea), and No. HR21C1003 (HR21C1003010021) awarded by Ministry of Health and Welfare (Republic of Korea).

CROSS REFERENCE TO RELATED APPLICATIONS

This application is a National Stage of International Application No. PCT/KR2018/008518 filed Jul. 27, 2018, claiming priority based on Korean Patent Application No. 10-2017-0096163 filed Jul. 28, 2017.

TECHNICAL FIELD

The present invention relates to a non-thermal atmospheric-pressure plasma keloid treatment device and a use thereof.

BACKGROUND ART

Keloid, which refers to a disease wherein fibrous tissues abnormally, densely grow during wound healing after skin damage, has a property of spreading to surrounding areas beyond the size of a wound or an inflamed area. Clinically, cases wherein the epidermis is normal, but the dermis is proliferated, thus being thick and vessel-rich, and infiltration of inflammatory cells increases compared to normal scar tissues are diagnosed as keloid. Collagen bundles in normal dermis are relaxed and distorted, whereas collagen bundles in keloids are thick and dense. Histologically, keloid results in large, broad, closely-aligned collagen fibers consisting of numerous fibrils, and thick and hyalinized collagen that is irregularly arranged in a spiral shape is called keloid collagen. Since such keloid wildly proliferates, it may cause cosmetic problems and, when generated at joints, may obstruct joint function. Therefore, it is most important for people with the potential for keloids to avoid injury. Until now, there is no way to prevent for inevitably occurred wounds from proceeding to keloids, so there is an urgent need for development thereof.

Plasma, which is an ionized gas that satisfies the Debye sheath in physics or chemistry, is an aggregate of charged particles having electrical conductivity. As attempts to apply plasma to the biomedical field, technologies such as "SKIN TREATMENT APPARATUS USING PLASMA (KR 10-1568380 B1)", "METHOD OF TREATING SKIN WITH PLASMA (U.S. Pat. No. 9,226,790 B2)", and "PLASMA APPARATUS FOR SKIN SURFACE MODIFICATION (U.S. Pat. No. 6,518,538 B2)" have been recently developed. However, there is no technology development regarding the treatment of keloids using plasma.

Therefore, the present invention relates to a plasma generation apparatus having a keloid prevention and treatment effect. Since a non-thermal atmospheric-pressure plasma keloid treatment device according to the present invention has effects of inhibiting collagen deposition in keloid fibroblasts and mobility thereof, it is expected to be widely used for the prevention and treatment of keloids.

DISCLOSURE

Technical Problem

Therefore, the present invention has been made in view of the above problems, and it is one object of the present invention to provide a non-thermal atmospheric-pressure plasma keloid treatment device and a use thereof.

It will be understood that technical problems of the present invention are not limited to the aforementioned problems and other technical problems not referred to herein will be clearly understood by those skilled in the art from disclosures below.

Technical Solution

Hereinafter, various embodiments described herein will be described with reference to the accompanying drawings. In the following description, for complete understanding of the present invention, various specific details, e.g., such as specific forms, compositions, processes, and the like, are described. However, certain embodiments may be implemented without one or more of these specific details or with other known methods and forms. In other embodiments, well-known process and manufacturing techniques are not described in specific forms, in order not to unnecessarily obscure the present invention. References throughout the specification for "one embodiment" or "an embodiment" mean that particular features, forms, compositions, or characteristics disclosed in connection with the embodiment are included in one or more embodiments of the present invention. Accordingly, "one embodiment" or "an embodiment" expressed in various parts throughout this specification does not necessarily represent the same embodiment of the present invention. Additionally, particular features, forms, compositions, or characteristics may be combined in any suitable manner in one or more embodiments.

In the present specification, "keloid" is a disease wherein fibrous tissues abnormally, densely grow during wound healing after skin damage, and is also called "benign dermal fibrous tumor". Keloid is caused by impairment in a function of properly regulating and inhibiting a wound healing process, is thought to be caused by abnormal accumulation of extracellular matrix (ECM) such as excessive secretion of collagen, and does not become malignant. Unlike normal scars, keloids are hard, protrude above the skin surface, and have red and irregular surfaces. Since keloids widely spread, they can cause cosmetic problems when occur on the face, and can cause movement disorders when occurring at important areas such as joints.

Keloids can infiltrate surrounding normal skin beyond an original wound unlike hypertrophic scars. Accordingly, it is necessary to distinguish keloids from hypertrophic scars. More particularly, keloids occur months after trauma, do not improve over time, spread to surrounding areas beyond an original lesion site, occur only in people with genetic factors, and occur in people with dark skin, whereas hypertrophic scars occur quickly after trauma, improve over time, are confined to wound sites, more frequently occur, and are not related to skin color.

In an embodiment of the present invention, "epidermal growth factor receptors (EGFR)" are receptors for extracellular protein ligands in the epidermal growth factor family and are present on cell surfaces. EGFR is a subfamily of four kinases (EGFR, HER2/c-neu, Her 3, and Her 4) with similar functions. EGFR is activated by binding to ligands such as epidermal growth factor (EGF) and transforming growth factor α. Such EGFR activation is very important for the endogenous immune response of epidermal cells.

Overexpression or overactivity of EGFR by mutation is associated with the development of cancers such as lung cancer, colorectal cancer, and glioblastoma multiforme and is also associated with keloid. The activity of EGFR was known to increase in fibroblasts from keloid skin.

In an embodiment of the present invention, "signal transducer and activator of transcription 3 (STAT3)" is an intercellular signal transducer and a transcription factor. A phosphorylated form of STAT3, pSTAT3 (phosphorylated STAT3), is well known to be delivered into a cell nucleus, and the expression of most proteins is regulated by pSTAT3.

In an embodiment of the present invention, "non-thermal atmospheric pressure plasma" is also referred to as cold or non-equilibrium plasma and is a concept opposite to thermal plasma. Non-thermal atmospheric pressure plasma can be easily produced with low energy under relatively low pressure. In the case of non-thermal atmospheric pressure plasma, the temperature of reaction gas is similar to that of the atmosphere, but electron temperature is about 10 to 100 times higher than the atmosphere temperature. Non-thermal atmospheric pressure plasma generates chemically highly reactive reactants at normal and high pressures, and thus can promote chemical reactions that are difficult or impossible to achieve by conventional methods.

In the present specification, "pharmaceutical composition" refers to a composition administered for a specific purpose. According to the purpose of the present invention, the pharmaceutical composition of the present invention is a composition including a product pretreated with the non-thermal atmospheric-pressure plasma keloid treatment device of the present invention and an expression inhibitor of EGFR or STAT3 gene as an effective ingredient. The composition may include related proteins and a pharmaceutically acceptable carrier, excipient, or diluent. The "pharmaceutically acceptable" carrier or excipient means those that are approved by the governmental regulatory authority or listed in the government or other generally approved pharmacopoeia for use in vertebrates and more particularly in humans.

For parenteral administration, the pharmaceutical composition of the present invention may be in the form of a suspension, solution or emulsion in an oily or aqueous carrier, and may be prepared in the form of a solid or a semisolid. In addition, the pharmaceutical composition of the present invention may include a formulating agent such as a suspending agent, a stabilizer, a solubilizer, and/or a dispersant and may be sterilized. The pharmaceutical composition may be stabilized under production and storage conditions, and may be preserved against the contaminating action of microorganisms such as bacteria or fungi. Alternatively, the pharmaceutical composition of the present invention may be provided in a sterile powder form for reconstitution with a suitable carrier prior to use. The pharmaceutical composition may be provided in a unit-dose form or in a microneedle patch from, or may be contained in ampoules, in other unit-dose containers, or in multi-dose containers. Alternatively, the pharmaceutical composition may only be stored in a sterile liquid carrier, for example in a freeze-dried form that requires the addition of water for injection just before use. Immediately injectable solutions and suspensions may be prepared from sterile powders, granules, or tablets.

In some non-limiting embodiments, the pharmaceutical composition of the present invention may be formulated or included in the form of microspheres in a liquid. In certain non-limiting embodiments, the pharmaceutical composition of the present invention may include a pharmaceutically acceptable compound and/or mixture at a concentration of 0.001 to 100,000 U/kg. In addition, in certain non-limiting embodiments, a suitable excipient of the pharmaceutical composition of the present invention may include a preservative, a suspending agent, an additional stabilizer, a dye, a buffer, an antibacterial agent, an antifungal agent, and an isotonic agent, for example, sugar or sodium chloride. As used herein, the term "stabilizer" refers to a compound optionally included in the pharmaceutical composition of the present invention to increase shelf lifespan. In a non-limiting embodiment, a stabilizer may be a sugar, an amino acid, or a polymer. In addition, the pharmaceutical composition of the present invention may include one or more pharmaceutically acceptable carriers. The carrier may be a solvent or a dispersion medium. Non-limiting examples of a pharmaceutically acceptable carrier include water, saline, ethanol, polyols (e.g., glycerol, propylene glycol, and liquid polyethylene glycols), oils, and suitable mixtures thereof. Non-limiting examples of a sterilization technique applied to the pharmaceutical composition of the present invention include filtration through a bacteria-inhibiting filter, terminal sterilization, incorporation of sterile preparations, irradiation, sterile gas irradiation, heating, vacuum drying, and freeze drying.

In the present specification, "administration" means introducing the composition of the present invention to a patient in any suitable way, and the route of administration of the composition of the present invention may be any general route as long as it can reach a target tissue. The pharmaceutical composition of the present invention may be applied through oral administration, intraperitoneal administration, intravenous administration, intramuscular administration, subcutaneous administration, intradermal administration, intranasal administration, pulmonary administration, rectal administration, intraluminal administration, intraperitoneal administration, or intradural administration, and most preferably by applying to the skin or through subcutaneous or intradermal injection, but the present invention is not limited thereto.

A treatment method according to the present invention may include administrating the pharmaceutical composition in a pharmaceutically effective amount. An effective amount according to the present invention may be controlled depending upon various factors such as the type of disease, the severity of disease, effective ingredients contained in a composition, the types and amounts of other ingredients, the type of formulation, the age, weight, general health state, sex, and diet of a patient, administration time, administration route, a secretion rate of a composition, a treatment period, and concurrent drugs.

In an embodiment of the present invention, provided is a non-thermal atmospheric-pressure plasma keloid treatment device including a power supply, a plasma generator, a gas supply path, and a housing, wherein the power supply includes a high-voltage transformer, the plasma generator includes an electrode, a metal electrode, a dielectric, and a reaction part, the plasma generator includes a non-thermal atmospheric-pressure plasma source with multiple nozzles, the dielectric is constituted of a quartz or ceramic tube, the non-thermal atmospheric-pressure plasma keloid treatment device uses argon and nitrogen gases, a required power of the non-thermal atmospheric-pressure plasma keloid treatment device is 10 to 50 kHz, and a power peak thereof is 0.1 to 10 kV.

In another embodiment of the present invention, provided is a pharmaceutical composition for preventing or treating keloids, including plasm generated by means of the non-thermal atmospheric-pressure plasma keloid treatment device; and an expression inhibitor of EGFR or STAT3 gene as an effective ingredient, wherein the expression inhibitor of EGFR or STAT3 gene is selected from a group consisting of antisense oligonucleotides, siRNA, shRNA and microRNA specific to EGFR or STAT3 gene.

In still another embodiment of the present invention, provided is a cosmetic composition for preventing or treating keloids, including plasm generated by means of the non-thermal atmospheric-pressure plasma keloid treatment device; and an expression inhibitor of EGFR or STAT3 gene as an effective ingredient, wherein the expression inhibitor of EGFR or STAT3 gene is selected from a group consisting of antisense oligonucleotides, siRNA, shRNA and microRNA specific to EGFR or STAT3 gene.

In still another embodiment of the present invention, provided is a method of preventing or treating keloids, the method including a step of treating the skin of a subject, except for humans, with plasma using the non-thermal atmospheric-pressure plasma keloid treatment device.

In still another embodiment of the present invention, provided is a method of preventing or treating keloids, the method including (a) a step of treating the skin of a subject, except for humans, with plasma using the non-thermal atmospheric-pressure plasma keloid treatment device; and (b) a step of treating an expression inhibitor of EGFR or STAT3 gene, wherein the expression inhibitor of EGFR or STAT3 gene of step (b) is selected from the group consisting of antisense oligonucleotides, siRNA, shRNA and microRNA specific to EGFR or STAT3 gene.

Hereinafter, each step of the present invention will be described in detail.

Advantageous Effects

The present invention relates to a non-thermal atmospheric-pressure plasma keloid treatment device and a use thereof. The non-thermal atmospheric-pressure plasma keloid treatment device according to the present invention has effects of inhibiting collagen deposition in keloid fibroblasts and mobility thereof, and thus, is expected to be greatly useful for preventing and treating keloids.

BEST MODE

Figure 1:
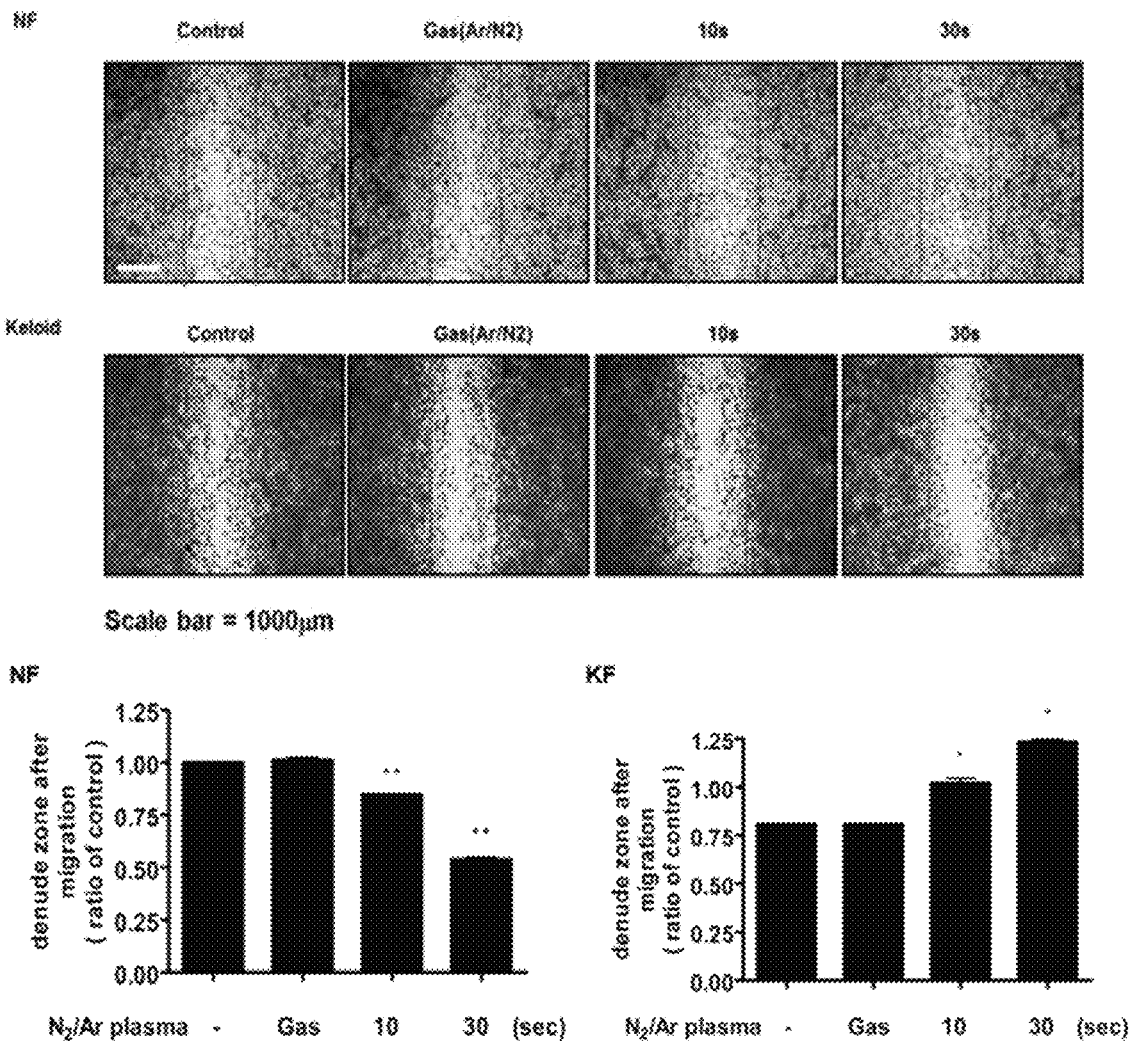
FIG. 1 illustrates results of cell mobility according to plasma treatment in NF and KF according to an embodiment of the present invention.

Hereinafter, the present invention will be described in more detail with reference to the following Examples. It will be apparent to those skilled in the art that Examples are merely for concretely explaining the invention and therefore, there is no intent to limit the invention to Examples.

Example 1. Manufacture of Non-Thermal Atmospheric-Pressure Plasma Keloid Treatment Device A non-thermal atmospheric-pressure plasma keloid treatment device including a power supply, a plasma generator, a gas supply path, and a housing was manufactured. Here, the plasma generator includes an electrode, a metal electrode, a dielectric, and a reaction part, the power supply includes a high-voltage transformer, the plasma generator includes a non-thermal atmospheric-pressure plasma source with multiple nozzles, and the dielectric is constituted of a quartz or ceramic tube. In a non-limiting embodiment, the plasma generator of the present invention may include a high-voltage LF power module with a pulse width modulation controller IC to produce plasma under atmospheric pressure.

When the plasma generator for treating keloids of the present invention is used to treat keloids, a required power is preferably 10 to 50 kHz, more preferably 20 to 30 kHz, most preferably 25 kHz. A power peak by the high-voltage transformer is preferably 0.1 to 10 kV, more preferably 1 to 5 kV, most preferably 3 kV. A gas used in the plasma generation apparatus is argon and nitrogen, but the present invention is not limited thereto.

Example 2. Confirmation of Effects of Non-Thermal Atmospheric-Pressure Plasma Keloid Treatment Device

Example 2-1. Culture of Normal Fibroblasts or Keloid Fibroblasts

Fibroblasts isolated from skin tissue, diagnosed as keloid, spread beyond an original wound boundary for one or more years even after a wounded skin tissue was recovered were termed "keloid fibroblasts (KF)." Fibroblasts isolated from normal skin tissue were used as a control and termed "normal fibroblasts (NF)."

KF and NF were cultured in RPMI-1640 medium containing % by volume of FBS and 1% by volume of an antibiotic/antimicrobial under 5% by volume of $CO_2$ in a 37° C. wet environment. Passage culture was performed when KF proliferated to a density of 80 to 90%. The passage was performed using trypsin. In examples of the present invention, cells of F2 to F7 generations were only used.

Example 2-2. Confirmation of Cell Mobility According to Plasma Treatment in NF and KF To investigate plasma effect on cell migration, as an important cellular mechanism in wound healing of NF and KF-mediated keloid formation, wound healing analysis was performed. For this, NF or KF were cultured at a density of $5 \times 10^5$/well in a 12-well culture plate. The center of cells forming a monolayer sheet was scraped with a tip, followed by washing to remove cell debris due to the scraping, treating with plasma for 10 or 30 seconds using nitrogen and argon gases, and additionally culturing for 24 hours, followed by measuring cell migration.

As experimental results, treatment with plasma for 10 seconds did not cause significant differences in both NF and KF, compared to a control (a non-treated group or a group treated only with gas). When treated with plasma for 30 seconds, migration of NF increased by 28% compared to a control, but migration of KF rather decreased by 36%. These results are shown in FIG. 1.

Example 2-3. Confirmation of Cell Viability According to Plasma Treatment in NF and KF Whether molecular mechanisms related to cell viability according to plasma treatment in NF and KF were changed was confirmed.

Figure 2A:
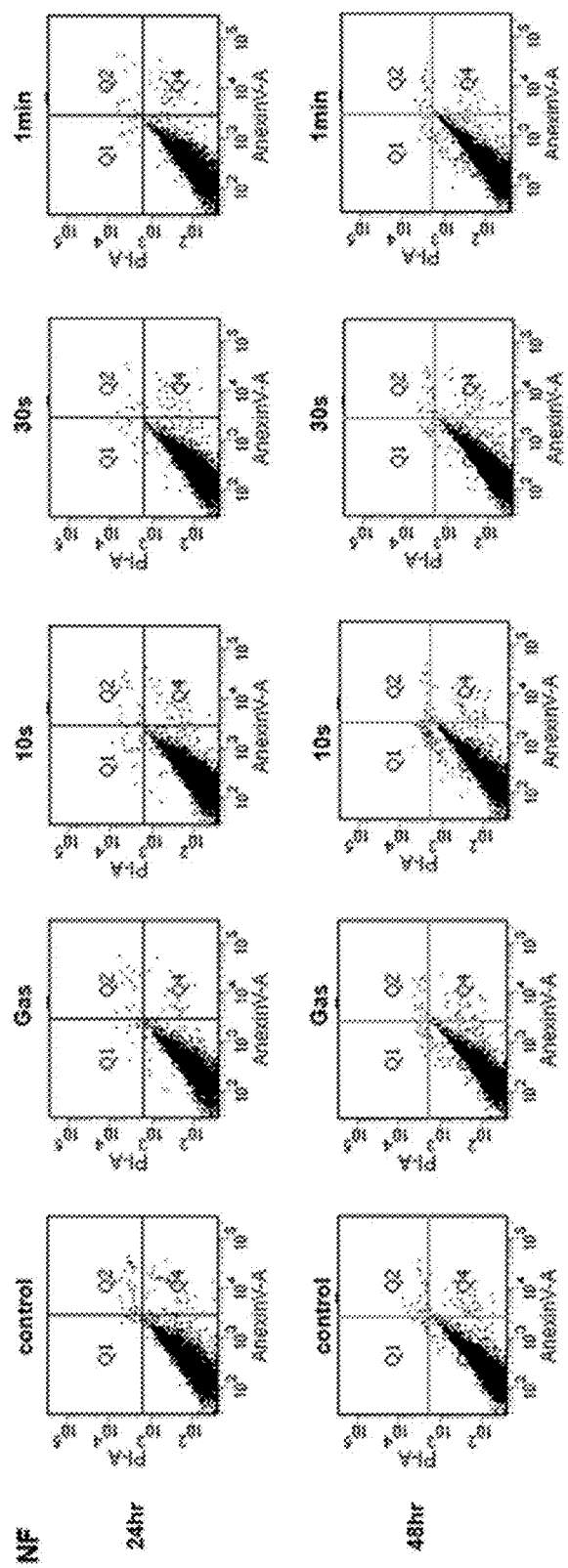
FIGS. 2A-2C illustrate results of FITC Annexin V/PI cell death staining performed to investigate cell viability changes according to plasma treatment in NF and KF according to an embodiment of the present invention.
Figure 2B:
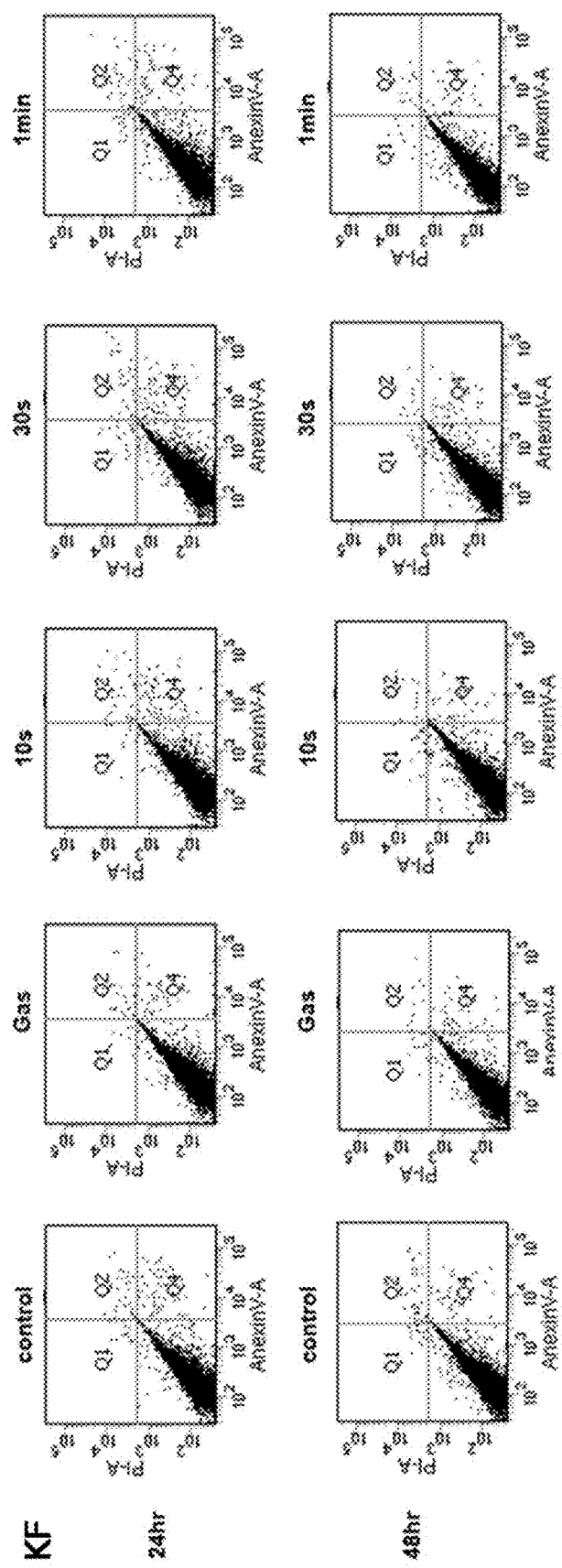
Figure 2C:
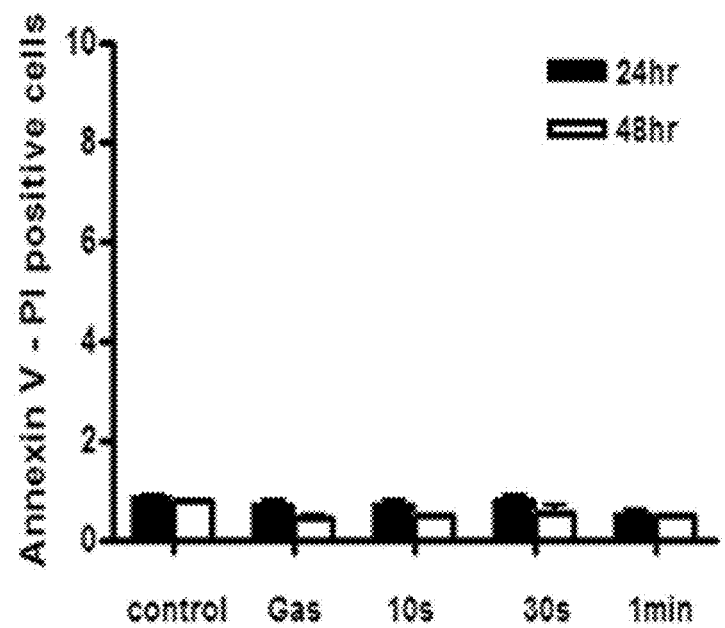
Figure 2C:
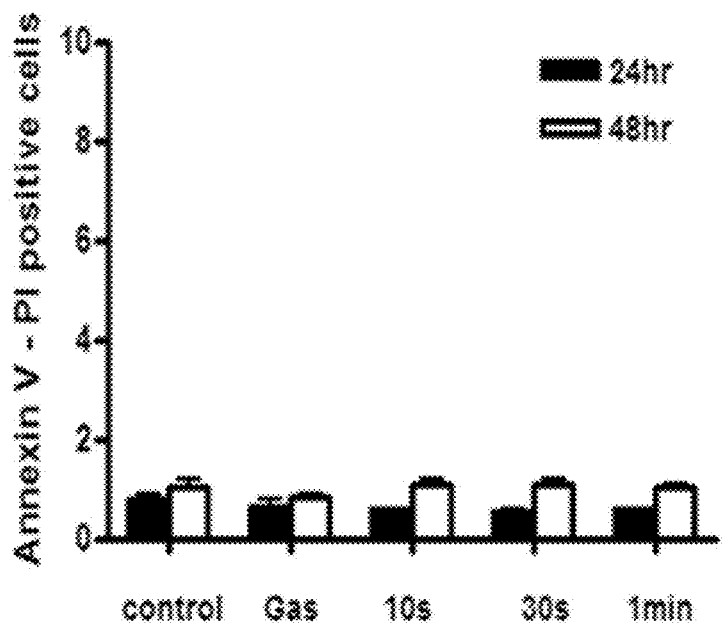

NF and KF were cultured and treated with plasma in the same manner as in Example 2-2 and were additionally cultured for 24 or 48 hours, followed by being subjected to FITC Annexin V/PI cell death staining (Annexin-V and propidium iodide staining, BD Biosciences) according to the manufacturer's protocol and being measured by means of a flow cytometer. Results are shown in FIGS. 2A-2C.

Figure 3:
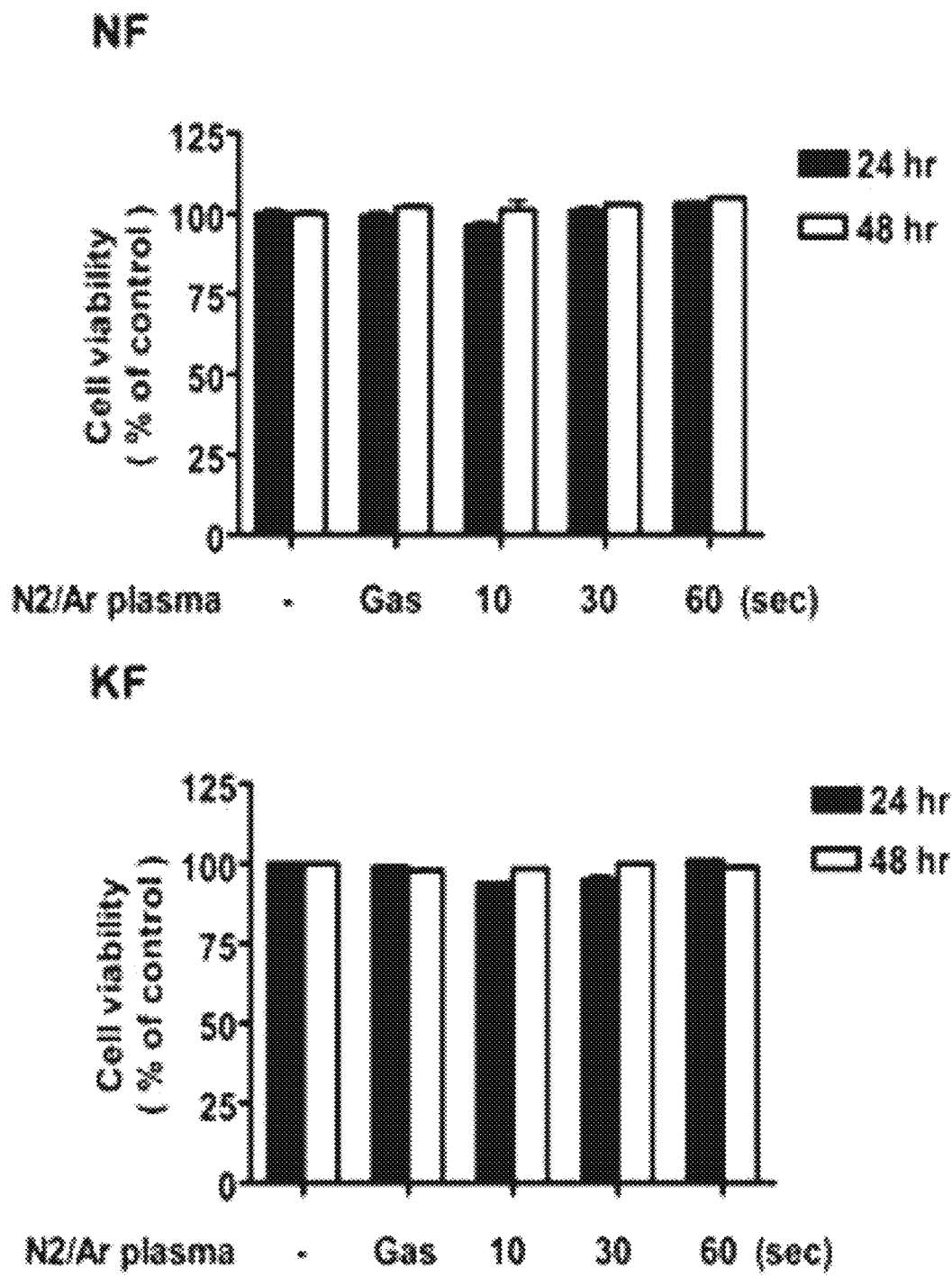
FIG. 3 illustrates results of MTT staining performed to investigate cell viability changes according to plasma treatment in NF and KF according to an embodiment of the present invention.

In addition, 3-(4,5-dimethylthiazol-2-yl)-2,5-diphenyl-tetrazoliumbromide (MTT, Sigma-Aldrich) staining was carried out to quantitatively measure cell proliferation rates. After staining, optical measurements were carried out at 540 nm using a microplate reader (Bio-Tek, Winooski, Vt., USA), and conversion into a percentage was made based on a control non-treated with plasma. Results are shown in FIG. 3.

From results of FIGS. 2A-2C and 3, it was confirmed that plasma treatment did not induce a quantitative increase in NF or KF cells and did not significantly affect cell viability.

Example 2-4. Confirmation of Protein Expression Changes According to Plasma Treatment in NF and KF NF and KF were cultured and treated with plasma (10 seconds, 30 seconds, or 60 seconds) in the same manner as in Example 2-2 to measure intercellular protein expression changes. As antibodies for Western blotting, EGFR, E-cadherin, p-STAT-3 (Y705), STAT-3, p-ERK, ERK, Collagen Type 1, and α-tubulin (Cell Signaling Technology, Danvers, Mass., 1:1000) were used, and immunofluorescence staining was carried out using an anti-p-STAT3 antibody to observe an intercellular position of p-STAT3.

Figure 4A:
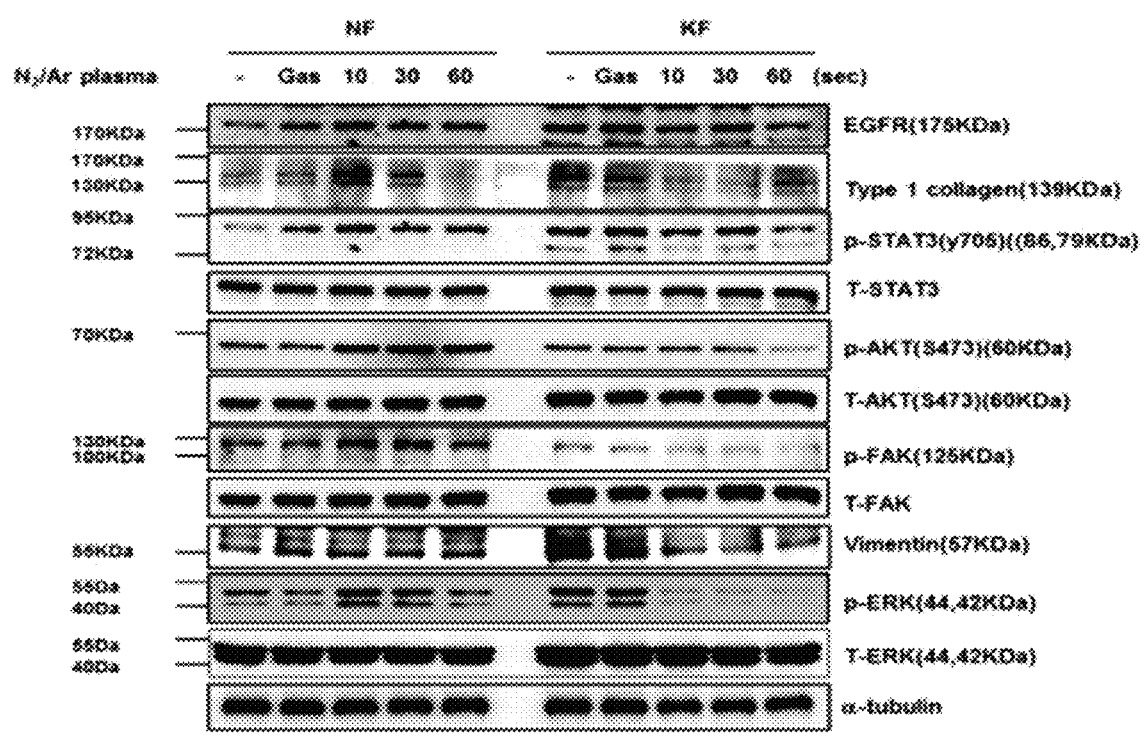
FIGS. 4A and 4B illustrate results of Western blotting performed to investigate protein expression changes according to plasma treatment in NF and KF according to an embodiment of the present invention.
Figure 4B:
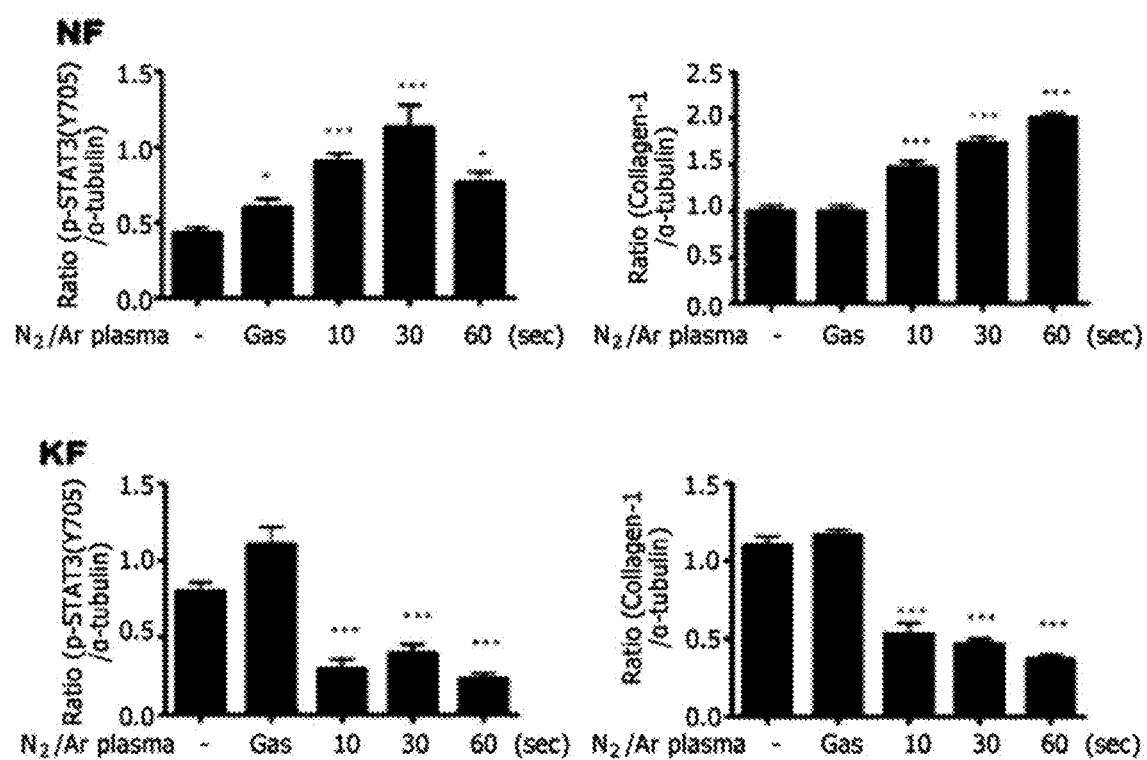
Figure 5:
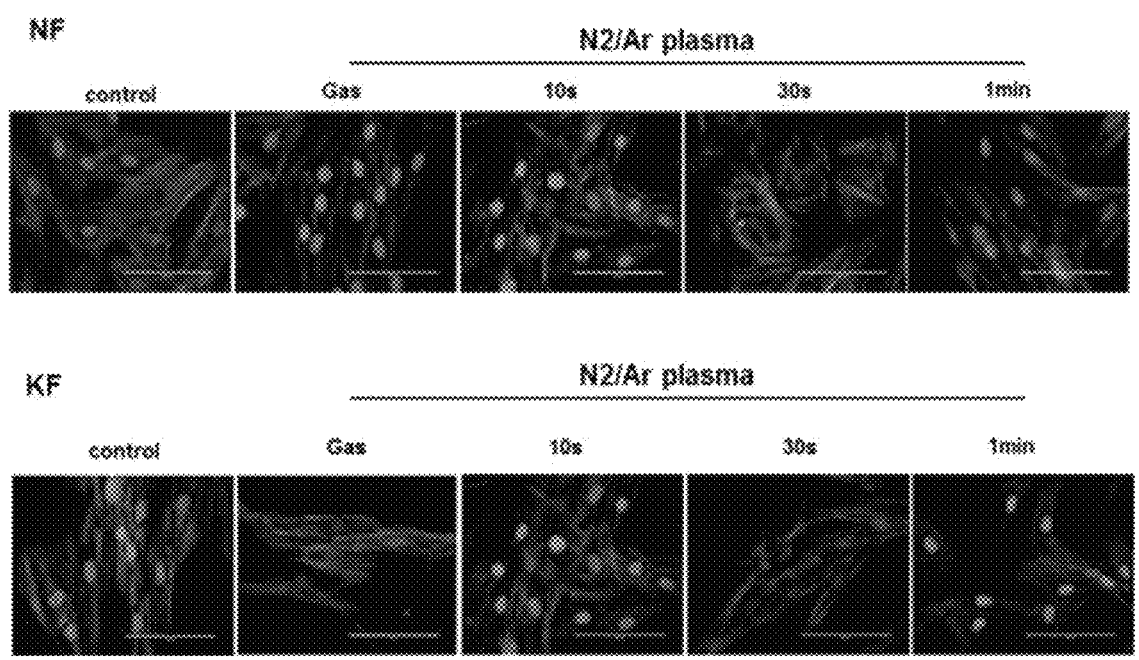
FIG. 5 illustrates results of immunofluorescence staining performed to investigate protein expression changes according to plasma treatment in NF and KF according to an embodiment of the present invention.

Western blotting results are shown in FIGS. 4A and 4B, and immunofluorescence staining results are shown in FIG. 5.

As experimental results, EGFR expression in NF treated with plasma was relatively maintained constant, but EGFR expression in KF treated with plasma was significantly reduced. The expression of E-cadherin was decreased in NF, but increased in KF. The expression level of p-ERK was not changed in NF, but was decreased in KF. Specifically, after being treated with plasma, the expression levels of p-STAT3 and Collagen Type 1 were higher in NF, but, compared to respective controls, were decreased in KF. Such results indicate that plasma treatment interferes with migration of keloid cells by inhibiting the pathways of EGFR, STAT3 and p-ERK in KF.

From immunofluorescence staining results, it was confirmed that plasma treatment caused a decrease in p-STAT3 expression in KF, but caused an increase in p-STAT3 expression in NF. However, translocation of STAT3 into a nucleus was not observed in any cell types.

Example 2-5. Confirmation of Migration Inhibition Mechanism in KF According to Plasma Treatment

Figure 6:
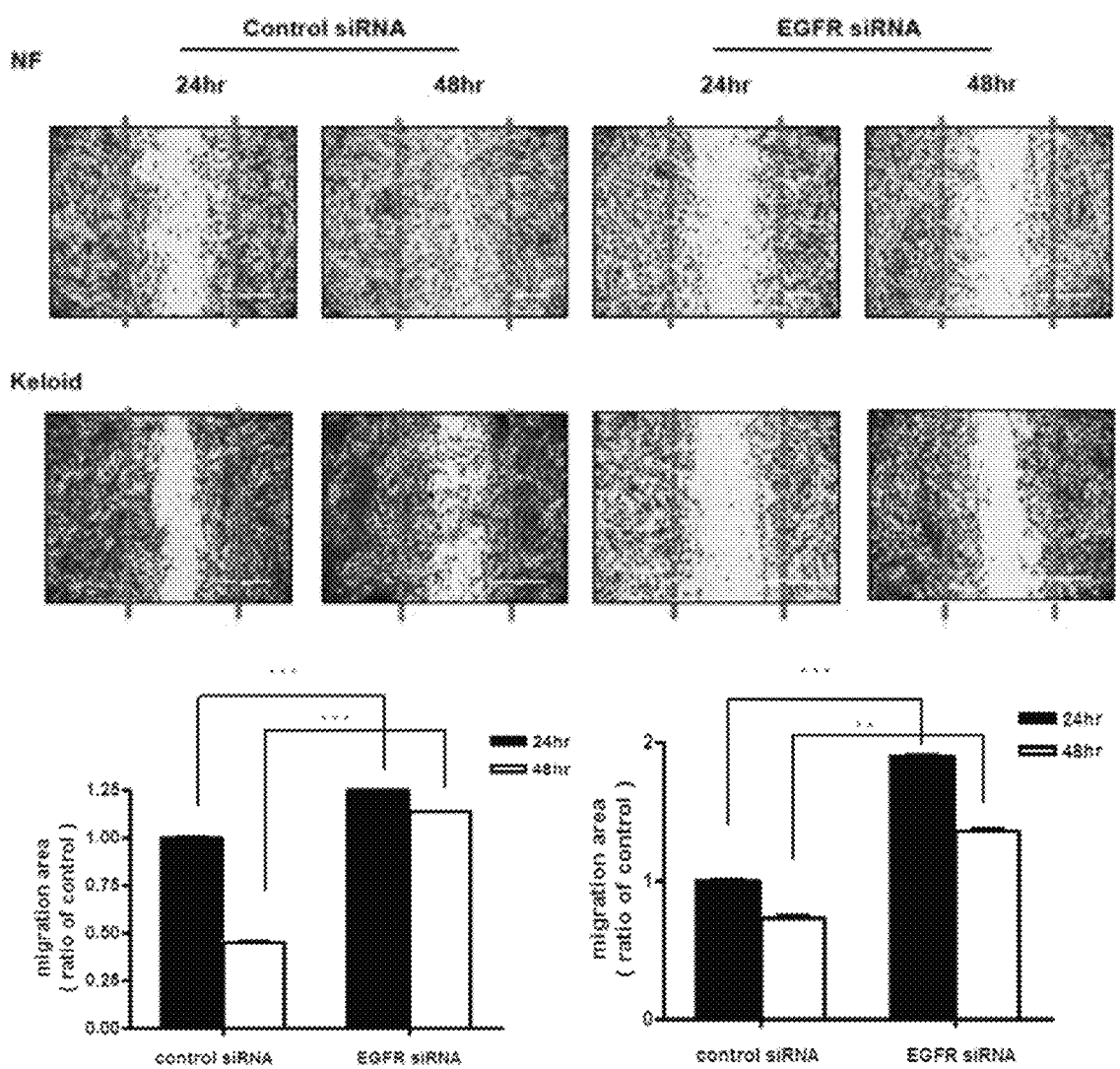
FIG. 6 illustrates cell mobility changes in NF and KF after being treated with EGFR-specific siRNA according to an embodiment of the present invention.
Figure 7:
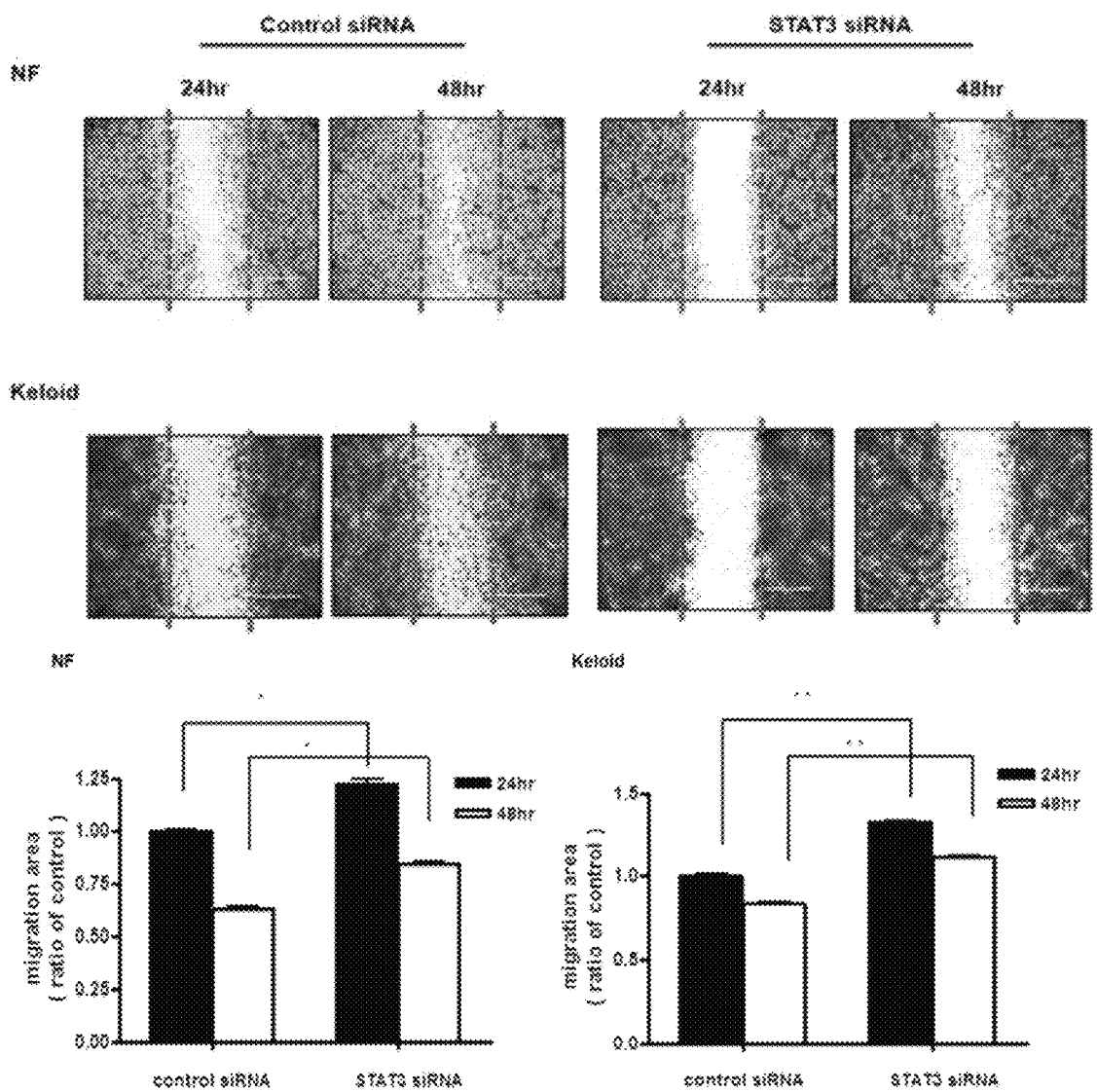
FIG. 7 illustrates cell mobility changes in NF and KF after being treated with STAT3-specific siRNA according to an embodiment of the present invention.
Figure 8:
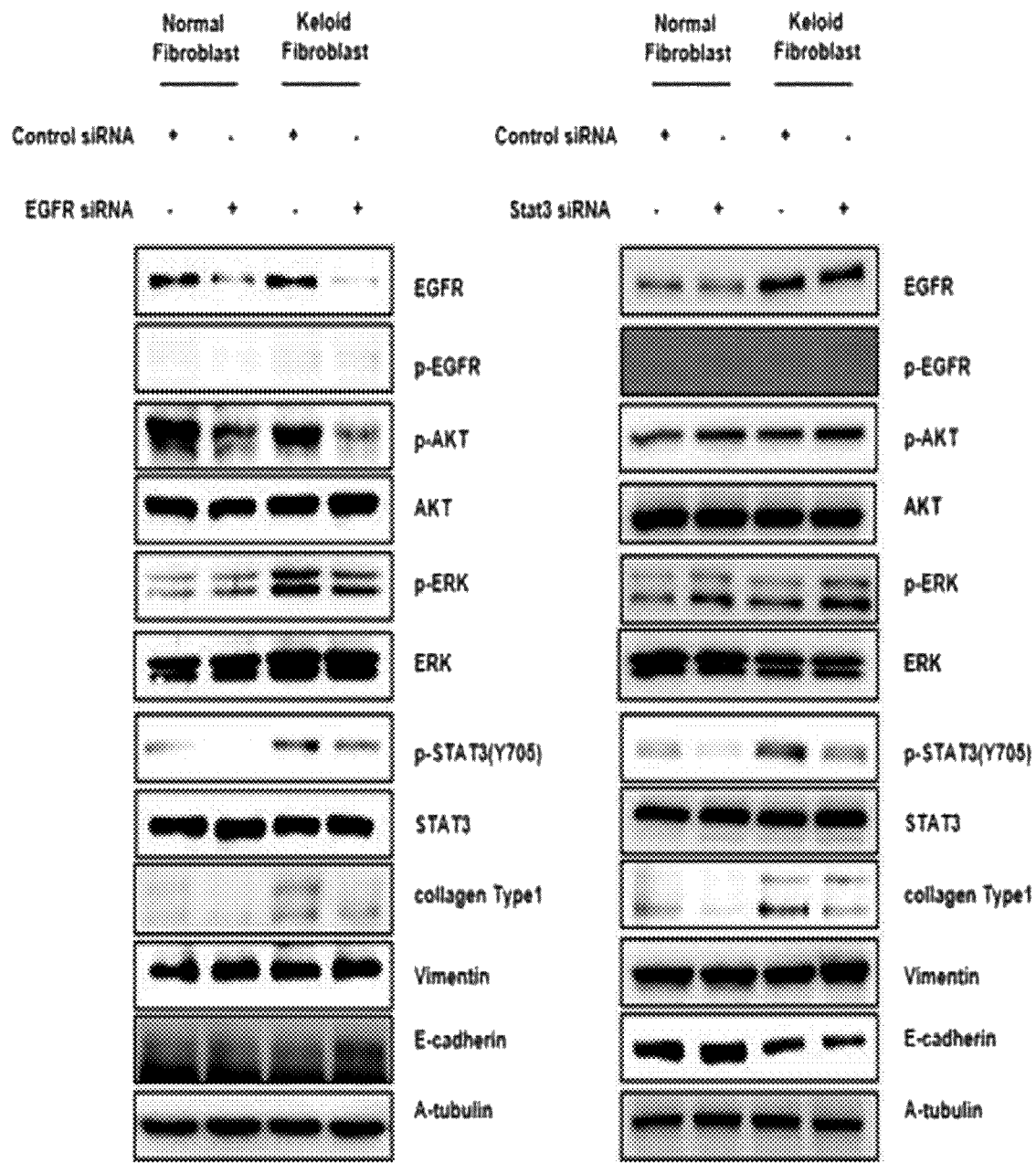
FIG. 8 illustrates protein expression changes in NF and KF after being treated with EGFR or STAT3-specific siRNA according to an embodiment of the present invention.

Example 2-5-1. Confirmation of Cell Migration Mechanism Using EGFR siRNA and STAT3 siRNA To assess the roles of EGFR and STAT3 in cell migration, NF and KF were treated with EGFR or STAT3-specific siRNA, and then cell mobility and protein expression changes were investigated. For transfection with siRNA, Lipofectamine 2000 (Gibco/Invitrogen) reagent was used, a medium was removed after culturing cells for 24 hours, and the cells were washed with PBS and treated with siRNA for 24 or 48 hours. EGFR-specific siRNA, STAT3-specific siRNA, and a control siRNA were obtained from Genolution Pharmaceuticals (Seoul, Korea). Cell mobility analysis was carried out in the same manner as in Example 2-2, and protein expression change analysis was carried out in the same manner as in Example 2-4 using EGFR, p-EGFR, p-AKT (Ser473), AKT, p-ERK, ERK, p-STAT-3 (Y705), STAT-3, Collagen Type 1, Vimentin, E-cadherin, and a-tubulin (Cell Signaling Technology, Danvers, Mass., 1:1000). Results of the EGFR-specific siRNA treatment are shown in FIG. 6, results of the STAT3-specific siRNA treatment are shown in FIG. 7, and results of the protein expression change analysis are shown in FIG. 8.

As experimental results, cell migration inhibition by EGFR-specific siRNA was effective in both NF and KF, and cell migration by STAT3-specific siRNA was also similarly inhibited in both NF and KF. From the protein expression change analysis, it was confirmed that the expressions of EGFR, p-AKT, p-STAT3, and Collagen Type 1 in NF and KF were reduced by treating with EGFR-specific siRNA. When STAT3-specific siRNA was simultaneously treated, the expression of Collagen Type 1 was reduced, but the expression levels of EGFR and p-AKT were not affected. Such results indicate that inhibition of EGFR and STAT3 may play a central epidemiological role in the inhibition of cell migration by plasma treatment.

Example 2-5-2. Confirmation of Cell Migration Mechanism in NF and KF Treated with Plasma Based on the results of Example 2-5-1, it was confirmed whether plasma treatment suppressed collagen generation in KF.

Figure 9:
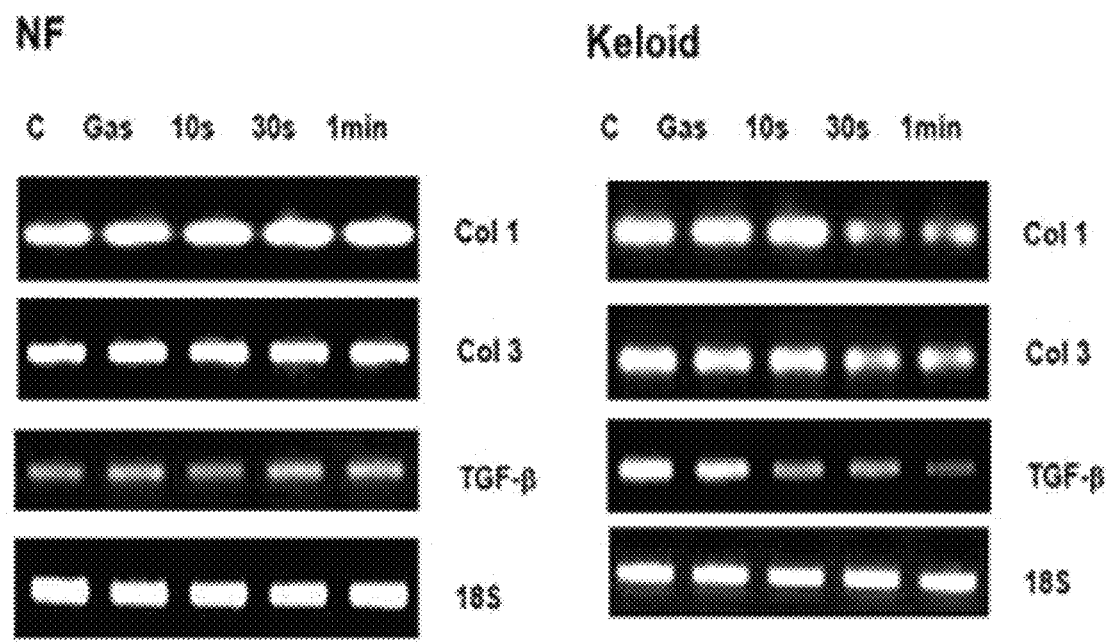
FIG. 9 illustrates results of RT-PCR performed to investigate expression changes in Collagen Type 1, Collagen Type 3 and TGF-β according to plasma treatment in NF and KF according to an embodiment of the present invention.

First, the expression levels of Collagen Type 1, Collagen Type 3 and TGF-β in NF and KF treated with plasma for 10 seconds, 30 seconds, or 60 seconds in the same manner as in Example 2-2 were assessed by RT-PCR. Collagen deposition increased through activation of TGF-β signal transduction represents a major mechanism of keloid formation. Primer sequences for RT-PCR are summarized in Table 1 below. Particularly, a sample was denatured at 94° C. for 3 minutes, and then amplified for 30 seconds at 94° C., 62° C. and 72° C., and then elongated for 5 minutes at 72° C. A final product was separated by electrophoresis on a 1.5% agarose gel, and bands were detected using ultraviolet light (Bio-Rad, Hercules, Calif., USA). Results are shown in FIG. 9.

TABLE 1

| Target gene | Direction | Sequence |
|---|---|---|
| Collagen Type 1 | F (forward direction) | 5'-GGG CAA GAC AGT GAT TGA ATA-3' (SEQ ID NO: 1) |
|  | R (reverse direction) | 5'-ACG TCC AAG CCG AAT TCC T-3' (SEQ ID NO: 2) |
| Collagen Type 3 | F (forward direction) | 5'-AGG TCC TGC GGG TAA CAC T-3' (SEQ ID NO: 3) |
|  | R (reverse direction) | 5'-ACT TTC ACC CTT GAC ACC CTG-3' (SEQ ID NO: 4) |
| TGF-β | F (forward direction) | 5'-CCG ACT ACT ACG CCA AGG-3' (SEQ ID NO: 5) |
|  | R (reverse direction) | 5'-AGT GAA CCC GTT GAT CA-3' (SEQ ID NO: 6) |
| GAPDH | F (forward direction) | 5'-ACC ACA GTC CAT GCC ATC AC-3' (SEQ ID NO: 7) |
|  | R (reverse direction) | 5'-TCC ACC ACC CTG TTG CTG TA-3' (SEQ ID NO: 8) |

As experimental results, the expression levels of Collagen Type 1, Collagen Type 3 and TGF-β mRNA in NF after being treated with plasma were not significantly changed. However, all of the three mRNA types in KF were significantly reduced.

Next, to investigate whether the deposition of soluble collagen at a cellular level by plasma treatment was reduced, total soluble collagen in a cell culture supernatant was quantified. For this, Sircol collagen assay (Biocolor, Belfast, UK) was carried out. Particularly, cells were cultured in a 60 mm$^2$ culture plate for 24 hours, 400 μl of Sirius red stain, as an anionic dye specifically reacting with a basic collagen side chain group, was added to a supernatant, and then additional culture was performed while gently rotating for 30 minutes at room temperature, and then centrifugation was performed at 12,000 g for 10 minutes, and then a collagen binding dye was re-dissolved after addition of 1 ml of 0.5 M NaOH, and then an absorbance at 540 nm was measured by enzyme-linked immunosorbent assay (Bio-Tek, Winooski, Vt., USA). Absorbance is directly proportional to the amount of collagen newly formed in a cell culture supernatant.

Figure 10:
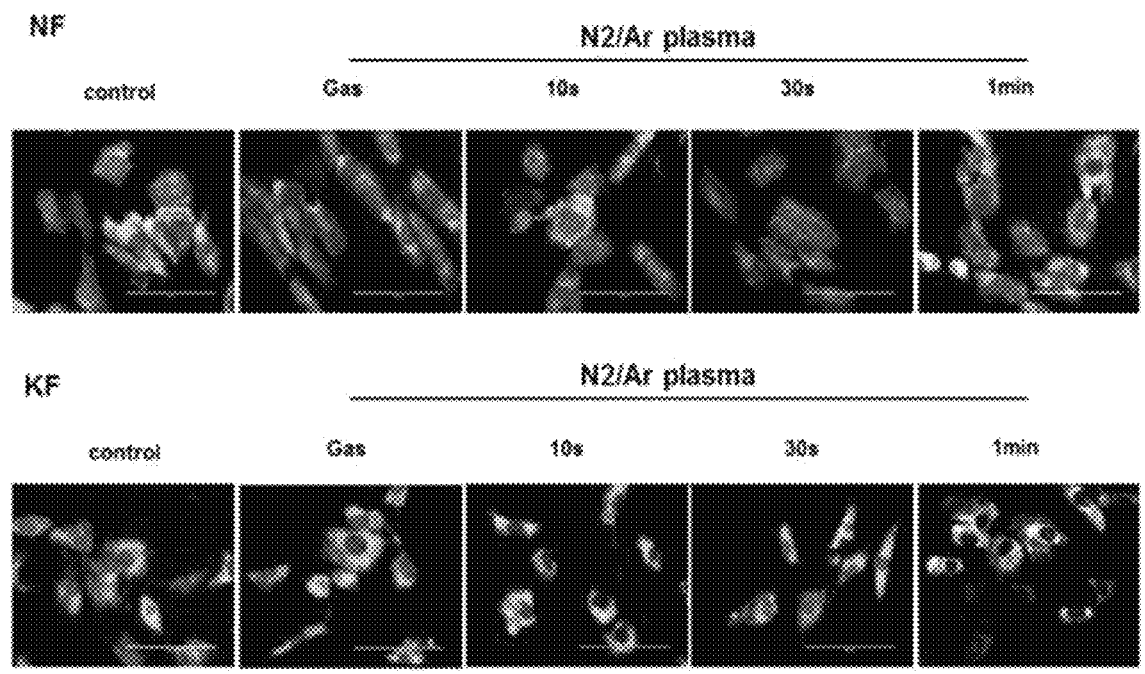
FIG. 10 illustrates results of Sircol collagen assay performed to investigate changes in collagen deposition levels according to plasma treatment in NF and KF according to an embodiment of the present invention.

As experimental results, it was confirmed that, by the plasma treatment, a soluble collagen content was slightly reduced in KF, but rather slightly increased in NF. Results are shown in FIG. 10.

Figure 11:
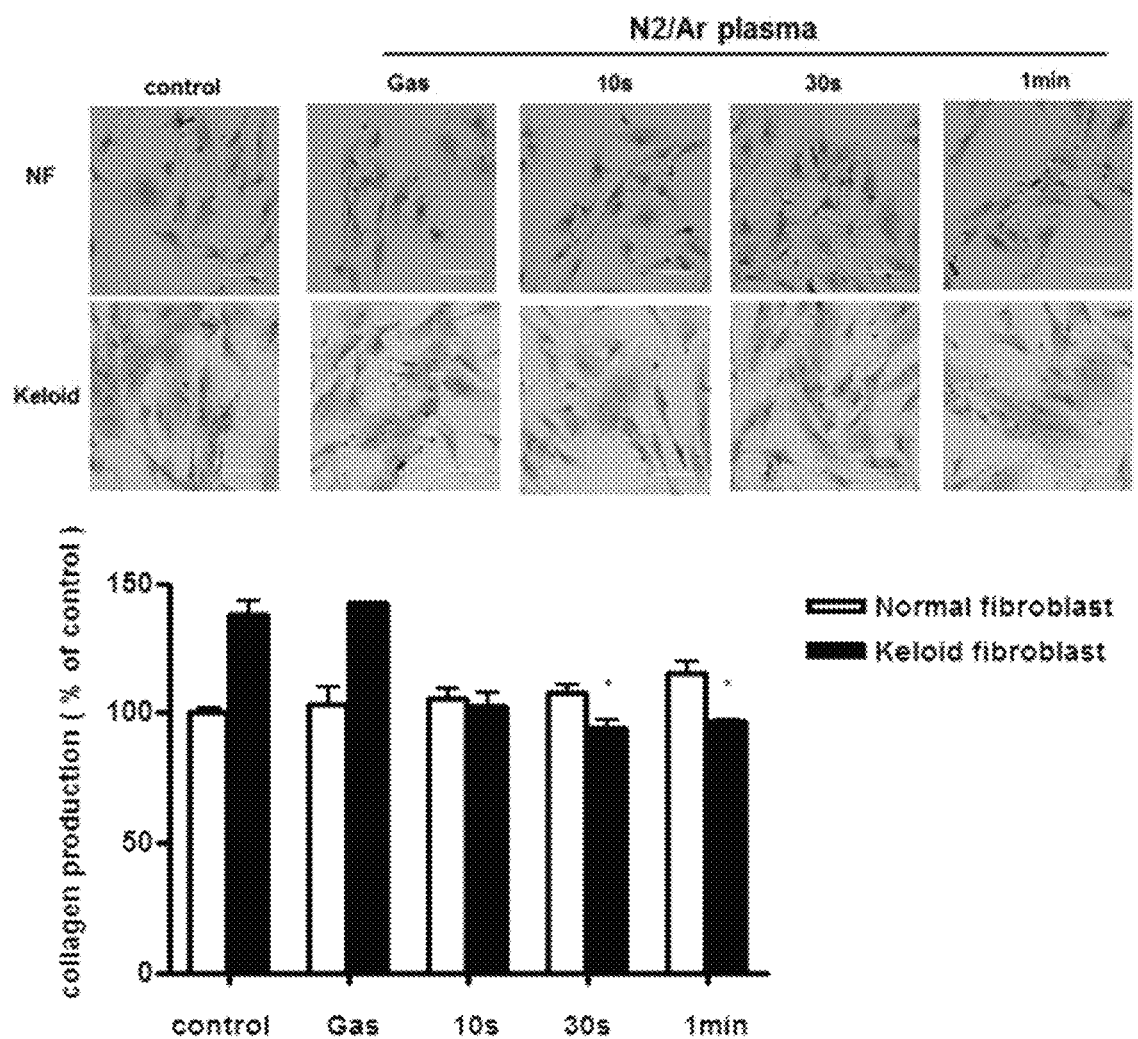
FIG. 11 illustrates results of immunofluorescence staining performed to investigate changes in collagen deposition levels according to plasma treatment in NF and KF according to an embodiment of the present invention.

In addition, it was confirmed that the expression level changes in Collagen Type 1 by the plasma treatment were the same as the immunofluorescence staining results. These results are shown in FIG. 11.

Figure 12:
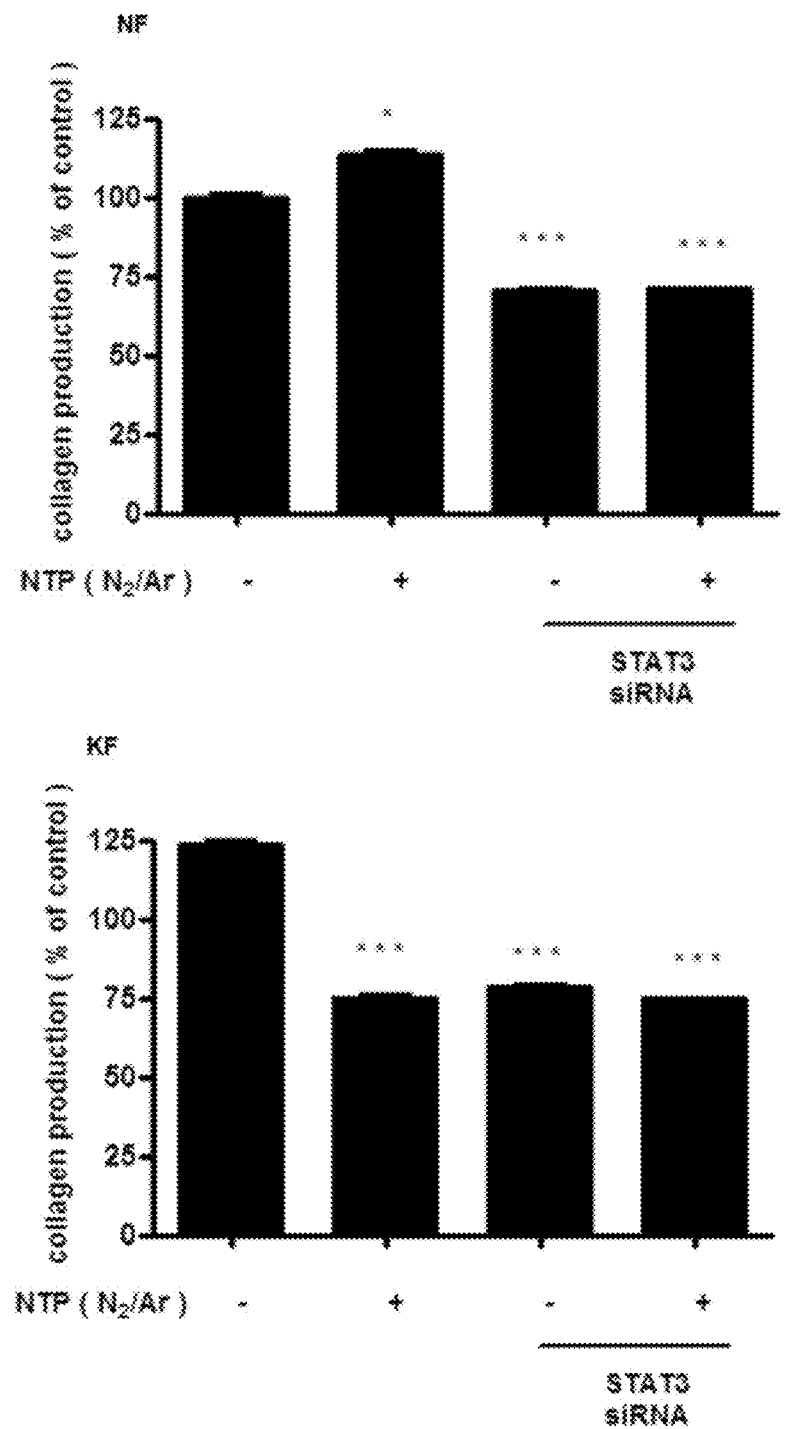
FIG. 12 illustrates changes in collagen deposition levels after treating NF and KF with a combination of plasma and STAT3-specific siRNA according to an embodiment of the present invention.

Example 2-6. Confirmation of Collagen Production Change in NF and KF Treated with Combination of Plasma and siRNA NF and KF were treated with a combination of plasma and STAT3-specific siRNA. As results, it was confirmed that, when treated with a combination of plasma and STAT3-specific siRNA, the generation of collagen was significantly reduced, compared to the cases of treating with only plasma or STAT3-specific siRNA. These results are shown in FIG. 12.

From the results of Examples 1 and 2, it was confirmed that cell mobility in KF was significantly reduced by plasma treatment, which was caused by collagen synthesis reduction in cells. In addition, it was confirmed that the generation of keloid could be further significantly inhibited when treated with a combination of plasma and STAT3-specific siRNA.

---

The invention claimed is:

1. A method of preventing or treating keloids of a subject in need thereof, the method comprising:
   (a) a step of treating a skin of the subject with plasma for at least 30 seconds using a non-thermal atmospheric-pressure plasma keloid treatment device,
      wherein the non-thermal atmospheric-pressure plasma keloid treatment device comprises
      a power supply;
      a plasma generator;
      a gas supply path; and
      a housing,
      wherein the power supply comprises a high-voltage transformer, the plasma generator comprises an electrode, a metal electrode, a dielectric, and a reaction part, the plasma generator comprises a non-thermal atmospheric-pressure plasma source with multiple nozzles, and the dielectric is constituted of a quartz or ceramic tube; and
   (b) a step of administering an expression inhibitor of EGFR or STAT3 gene to the subject.

2. The method according to claim 1, wherein the expression inhibitor of EGFR or STAT3 gene of step (b) is selected from the group consisting of antisense oligonucleotides, siRNA, shRNA, and microRNA specific to EGFR or STAT3 gene.

3. The method according to claim 2, wherein the non-thermal atmospheric-pressure plasma keloid treatment device has a required power of 10 to 50 kHz and a power peak of 0.1 to 10 kV.

4. The method according to claim 1, wherein the non-thermal atmospheric-pressure plasma keloid treatment device uses argon and nitrogen gases.

5. The method according to claim 1, wherein the non-thermal atmospheric-pressure plasma keloid treatment device has a required power of 10 to 50 kHz and a power peak of 0.1 to 10 kV.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Artificial
<220> FEATURE:
<223> OTHER INFORMATION: Collagen Type 1_F

<400> SEQUENCE: 1
gggcaagaca gtgattgaat a                    21

```
<210> SEQ ID NO 2
<211> LENGTH: 19
<212> TYPE: DNA
<213> ORGANISM: Artificial
<220> FEATURE:
<223> OTHER INFORMATION: Collagen Type 1_R

<400> SEQUENCE: 2
acgtccaagc cgaattcct                                                  19

<210> SEQ ID NO 3
<211> LENGTH: 19
<212> TYPE: DNA
<213> ORGANISM: Artificial
<220> FEATURE:
<223> OTHER INFORMATION: Collagen Type 3_F

<400> SEQUENCE: 3
aggtcctgcg ggtaacact                                                  19

<210> SEQ ID NO 4
<211> LENGTH: 21
<212> TYPE: DNA
<213> ORGANISM: Artificial
<220> FEATURE:
<223> OTHER INFORMATION: Collagen Type 3_R

<400> SEQUENCE: 4
actttcaccc ttgacaccct g                                               21

<210> SEQ ID NO 5
<211> LENGTH: 18
<212> TYPE: DNA
<213> ORGANISM: Artificial
<220> FEATURE:
<223> OTHER INFORMATION: TGF-beta_F

<400> SEQUENCE: 5
ccgactacta cgccaagg                                                   18

<210> SEQ ID NO 6
<211> LENGTH: 17
<212> TYPE: DNA
<213> ORGANISM: Artificial
<220> FEATURE:
<223> OTHER INFORMATION: TGF-beta_R

<400> SEQUENCE: 6
agtgaacccg ttgatca                                                    17

<210> SEQ ID NO 7
<211> LENGTH: 20
<212> TYPE: DNA
<213> ORGANISM: Artificial
<220> FEATURE:
<223> OTHER INFORMATION: GAPDH_F

<400> SEQUENCE: 7
accacagtcc atgccatcac                                                 20

<210> SEQ ID NO 8
<211> LENGTH: 20
<212> TYPE: DNA
<213> ORGANISM: Artificial
<220> FEATURE:
```

```
<223> OTHER INFORMATION: GAPDH_R

<400> SEQUENCE: 8
tccaccaccc tgttgctgta                                                    20
```